United States Patent
Shah et al.

(10) Patent No.: US 11,134,899 B2
(45) Date of Patent: Oct. 5, 2021

(54) CATHETER WITH SHUNTING ELECTRODE

(71) Applicant: Biosense Webster (Israel) Ltd., Yokneam (IL)

(72) Inventors: Kruti Shah, Mission Viejo, CA (US); Alexander Lifshitz, Arcadia, CA (US); Jerry Schmidt, Coto de Caza, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1140 days.

(21) Appl. No.: 15/148,475

(22) Filed: May 6, 2016

(65) Prior Publication Data

US 2017/0319144 A1    Nov. 9, 2017

(51) Int. Cl.
| | |
|---|---|
| *A61B 5/00* | (2006.01) |
| *A61B 18/14* | (2006.01) |
| *A61M 3/02* | (2006.01) |
| *A61B 18/00* | (2006.01) |
| *A61B 5/06* | (2006.01) |
| *A61B 5/318* | (2021.01) |
| *A61B 5/053* | (2021.01) |

(52) U.S. Cl.
CPC ............ *A61B 5/7217* (2013.01); *A61B 5/318* (2021.01); *A61B 5/6852* (2013.01); *A61B 5/6856* (2013.01); *A61B 18/1492* (2013.01); *A61M 3/0254* (2013.01); *A61B 5/053* (2013.01); *A61B 5/062* (2013.01); *A61B 2018/00011* (2013.01); *A61B 2018/00029* (2013.01); *A61B 2018/00351* (2013.01); *A61B 2018/00577* (2013.01); *A61B 2018/00839* (2013.01); *A61B 2018/1472* (2013.01); *A61B 2218/002* (2013.01)

(58) Field of Classification Search
CPC ... A61B 5/7217; A61B 5/0402; A61B 5/6852; A61B 5/6856; A61B 18/1492
See application file for complete search history.

(56) References Cited

U.S. PATENT DOCUMENTS

| | | | |
|---|---|---|---|
| 6,064,905 A | 5/2000 | Webster | |
| 6,080,151 A * | 6/2000 | Swartz | ............... A61B 18/1492 606/45 |
| 6,226,542 B1 | 5/2001 | Reisfeld | |
| 6,301,496 B1 | 10/2001 | Reisfeld | |
| 6,814,733 B2 | 11/2004 | Schwartz | |

(Continued)

FOREIGN PATENT DOCUMENTS

| | | | |
|---|---|---|---|
| EP | 1371339 | 12/2003 | |
| EP | 1371339 A1 * | 12/2003 | ......... A61B 18/1492 |
| EP | 2818128 | 12/2014 | |

OTHER PUBLICATIONS

European Search Report and Written Opinion for European Applicaion No. 17169635.4, dated Sep. 18, 2017.

*Primary Examiner* — Linda C Dvorak
*Assistant Examiner* — Annabeth E Rodriguez
(74) *Attorney, Agent, or Firm* — Dergosits & Noah LLP; Todd A. Noah

(57) ABSTRACT

A catheter with an electrode assembly has a functional electrode located at a first position on the electrode assembly and a shunting electrode located proximal to the first position. Irrigation fluid carried by the catheter may be electrically coupled with a patient's blood through the shunting electrode. The shunting electrode may be used to reduce noise in an electrocardiogram signal that results from the pump used to supply the irrigation fluid.

7 Claims, 3 Drawing Sheets

(56) References Cited

U.S. PATENT DOCUMENTS

| | | |
|---|---|---|
| 6,892,091 B1 | 5/2005 | Ben-Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 8,475,450 B2 * | 7/2013 | Govari ................. A61B 5/0422 600/374 |
| 8,956,353 B2 | 2/2015 | Govari |
| 2005/0273095 A1 * | 12/2005 | Taimisto ............ A61B 18/1492 606/41 |
| 2010/0168821 A1 * | 7/2010 | Johnson ............. A61B 18/1492 607/63 |
| 2013/0338467 A1 * | 12/2013 | Grasse .................. A61B 5/042 600/373 |
| 2014/0378805 A1 | 2/2014 | Ashton |

* cited by examiner

CATHETER WITH SHUNTING ELECTRODE

FIELD OF THE PRESENT DISCLOSURE

This invention relates to electrophysiologic (EP) catheters for mapping and/or ablation in the heart, in particular, to a catheter having a shunting electrode to reduce noise in an electrocardiogram (ECG) signal.

BACKGROUND

Medical catheterizations are routinely carried out today. For example, in cases of cardiac arrhythmias, such as atrial fibrillation, which occur when regions of cardiac tissue abnormally conduct electric signals. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

During ablation, the tissue is heated sufficiently to cause cellular destruction at the treatment site to form a lesion which is electrically non-conductive. However, overheating of tissue may cause the formation of char and coagulum and even steam pops. Overheated areas may also exhibit high impedance, resulting in a functional barrier to the passage of heat, interfering with the lesion creation. Despite the drawbacks associated with overheating, it is desirable to create a sufficiently large lesion to effectively ablate an abnormal tissue focus or block an aberrant conduction pattern. Creation of too small a lesion renders the medical procedure less effective or increases the time required. Therefore, to manage the heat produced and maintain the electrodes at an appropriate temperature to prevent overheating of tissue, the EP catheter may be irrigated. For example, commonly assigned U.S. Pat. No. 8,956,353, which is herein incorporated by reference, discloses the use of an irrigation pump to direct fluid through a lumen of the catheter in order to cool the ablation site.

Although irrigation is beneficial in managing heat, the system used to supply the fluid may result in unwanted noise in the intracardiac ECG signal. Notably, the peristaltic pump conventionally used in EP procedures generates static electricity due to friction between the irrigation tubing and the pump track as a result of the triboelectric effect. The static electricity manifests as noise in the ECG signal and the amplitude of the noise increases with the flow rate due to the higher motor speed. Attempts to suppress the noise due to the irrigation pump have involved modifications to the pump mechanics, but these techniques are not completely effective, particularly at higher irrigation flow rates that may be required to supply catheters having multiple ablation electrodes. Other attempts to reduce ECG noise employ additional cables or wires to ground the irrigation fluid, such as those described in U.S. Patent Publication No. 2014/0378805, hereby incorporated by reference in its entirety, which adds to the complexity of the system and requires management by the electrophysiologist.

Accordingly, it would be desirable to provide a catheter design that reduces ECG noise caused by the irrigation system. Further, it would be desirable to effectively reduce ECG noise at flow rates required to cool catheters having multiple ablation electrodes. The techniques of this disclosure as described in the following materials satisfy these and other needs.

SUMMARY

The present disclosure is directed to a catheter having an elongated catheter body with proximal and distal ends, an irrigation lumen extending through the elongated catheter body and an electrode assembly at the distal end of the catheter body. The electrode assembly may include a functional electrode located at a first position on the electrode assembly and a shunting electrode located proximal to the first position. The functional electrode and the shunting electrode are electrically coupled to irrigation fluid contained within the irrigation lumen.

In one aspect, the shunting electrode may be configured to form an electrical circuit between blood surrounding the shunting electrode when the electrode assembly is deployed in a patient's vasculature and irrigation fluid contained within the irrigation lumen.

In one aspect, the functional electrode may be an irrigated electrode supplied with irrigation fluid by the irrigation lumen. The electrode assembly may have a plurality of irrigated electrodes located distally of the first position.

In one aspect, the electrode assembly may also have at least one additional functional electrode located distally of the shunting electrode.

In one aspect, the shunting electrode may be spaced a distance corresponding to a distance of at least two of the irrigated electrodes from the first position.

In one aspect, the shunting electrode may be spaced a distance of at least 6 mm from the first position.

This disclosure also includes a method for treatment that may involve providing a catheter having an elongated catheter body with proximal and distal ends, a single irrigation lumen extending through the elongated catheter body and an electrode assembly at the distal end of the catheter body, the electrode assembly comprising a functional electrode located at a first position on the electrode assembly and a shunting electrode located proximal to the first position, advancing the distal end of the catheter with the electrode assembly to a desired region within a patient, supplying irrigation fluid through the irrigation lumen and electrically coupling the irrigation fluid with blood in the desired region within the patient through the shunting electrode.

In one aspect, supplying irrigation fluid through the irrigation lumen may involve operating a peristaltic pump.

In one aspect, electrocardiogram signals may be received with the electrode assembly. Electrically coupling the irrigation fluid with the patient, such as through blood and/or tissue, may reduce noise in the electrocardiogram signals resulting from the peristaltic pump.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
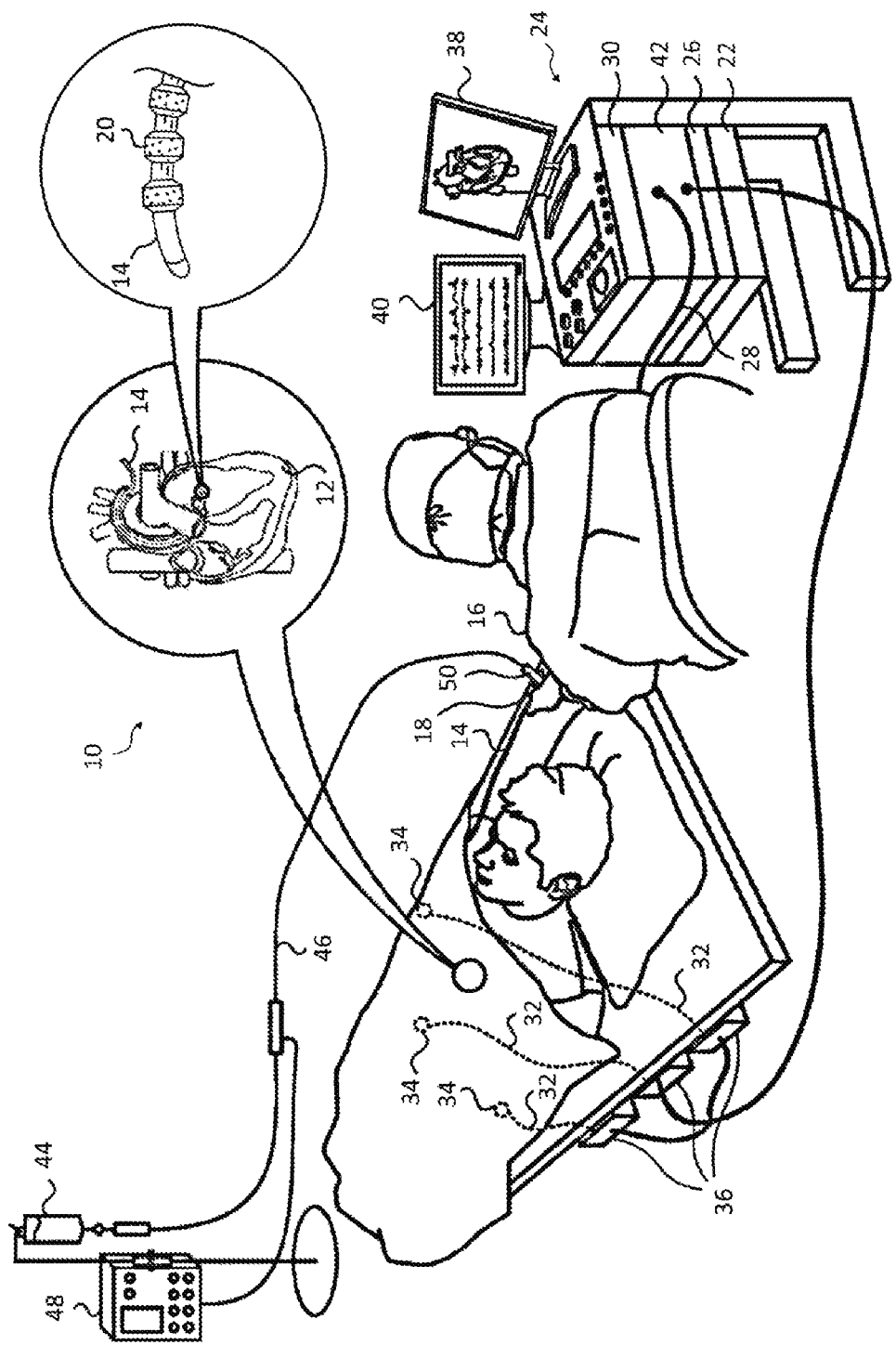
FIG. 1 is a schematic pictorial illustration of a system for ablation of tissue in the heart, according to one embodiment.

To help illustrate aspects of this disclosure, FIG. 1 is a pictorial illustration of a system 10 for performing exemplary catheterization procedures on a heart 12 of a patient. The system comprises a catheter 14, which is percutaneously inserted by an operator 16 through the patient's vascular system into a chamber or vascular structure of the heart 12. The catheter 14 typically comprises a handle 18, having suitable controls on the handle to enable the operator 16 to steer, position and orient the distal end of the catheter as desired for the ablation.

The operator 16, who is typically a physician, brings one or more electrodes 20, which may be perforated to supply irrigation fluid, into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226,542, and 6,301,496, and in commonly assigned U.S. Pat. No. 6,892,091, whose disclosures are herein incorporated by reference. To aid the operator 16, the distal portion of the catheter 14 contains position sensors (not shown) that provide signals to the processor 22, located in the console 24. One commercial product embodying elements of the system 10 is available as the CARTO® 3 System, available from Biosense Webster, Inc. (Diamond Bar, CA), which is capable of producing electroanatomic maps of the heart as required. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current from a radiofrequency (RF) generator 26 through wires in the catheter to one or more of the electrodes 20 positioned on a distal portion of the catheter 14, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia Ablation energy and electrical signals may be conveyed to and from the heart 12 through the catheter and the electrodes 20 via cable 28 to the console 24. Catheter 14 may also include one or more temperature sensors (not shown), typically a thermocouple or thermistor. The console 24 typically contains one or more ablation power generators 30. The catheter 14 may be adapted to conduct ablative energy to the heart using radiofrequency energy. Such methods are disclosed in commonly assigned U.S. Pat. Nos. 6,814,733, 6,997,924, and 7,156,816, which are herein incorporated by reference. Pacing signals and other control signals may be also conveyed from the console 24 through the cable 28 and the electrodes 20 to the heart 12.

Wire connections 32 may be used to link the console 24 with body surface electrodes 34 and other components of a positioning subsystem. Catheter electrodes and the body surface electrodes 34 may be used to measure tissue impedance at the ablation site as taught in U.S. Pat. No. 7,536,218, issued to Govari et al., which is herein incorporated by reference. Processor 22 may also be used to implement aspects of the positioning subsystem to measure location and orientation coordinates of the catheter 14. In one embodiment, the positioning subsystem comprises a magnetic position tracking arrangement that determines the position and orientation of the catheter 14 by generating magnetic fields in a predefined working volume and sensing these fields at the catheter, using field generating coils 36. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. The processor 22 is typically a computer with appropriate signal processing circuits. The processor 22 is coupled to drive a monitor 38. The signal processing circuits typically receive, amplify, filter and digitize signals from the catheter 14, including signals generated by the above-noted sensors and a plurality of location sensing electrodes (not shown) located distally in the catheter 14. The digitized signals are received via cable 28 and used by the console 24 and the positioning system to compute the position and orientation of the catheter 14 and analyze the electrical signals from the electrodes, and generate desired electroanatomic maps. The system 10 may also include an electrocardiogram (ECG) monitor 40, coupled to receive signals from one or more body surface electrodes. The ECG signal is typically received through an interface with the console 24, e.g., a patient interface unit 42 having an analog input and an isolated ground may be used to provide an ECG synchronization signal to the console 24.

To cool electrodes 20 during an ablation procedure, an electrically conductive fluid, e.g., saline, Ringer's lactate, may be delivered through a lumen in catheter 14 from a reservoir 44 via a hydraulic line 46. The electrically conductive fluid, which may be referred to herein as "saline" for convenience, it being understood that this is by way of example and not of limitation. The lumen of catheter 14 is in fluid communication with the perforations in electrodes 20, through which the saline may emerge to cool the electrode and the ablation site. A peristaltic pump 48 is connected to the hydraulic line 46 and causes the fluid to be delivered to the catheter 14 through an entrance port 50 at a desired rate. As noted above, operation of equipment in the environment, e.g., the pump 48, may produce electrical effects that result in noise or other interference with the ECG. The electrical emissions or signals are usually observed in ECG leads connected to a patient who is being transfused or infused with the electrically conductive solution. Any currents that flow in the patient's body as a result of this potential are sensed as characteristic noise added to the ECG signals.

Notably, pump 48 may be a source of electrical noise, created by a triboelectric effect that is associated with an induced charge being created on elements of the pump system, such as the surface of flexible tubing used in the pump, the pump track surface, the rotor surfaces used to compress the tubing and/or other structures. The rubbing or deforming action of the rotor against the tubing surface displaces electrical charge. Some of the charge is collected on the rotor and some is collected on the tubing surface. The tubing wall is generally an insulator, so that the external charge on the outside surface of the tube is induced on the inside of the tubing bore if the fluid in the tubing is an electrical conductor. In consequence, a generator potential appears between the electrically conductive fluid and the pump rotor.

Any electrical circuit between the saline, the pump and the patient's body allows current to flow. For example, a circuit may be formed sequentially from the pump 48, the irrigation lumen of the catheter 14, the irrigated functional electrodes 20, the blood, the patient's body, and the return path of the console 24 to ground. Such current, if sensed or intercepted by the ECG circuitry, produces undesirable signals on the ECG tracing that are perceived as "ECG noise" by the operator. Because the triboelectric potential is associated with the external and internal tubing walls, which are generally insulators (plastic), the triboelectric current has spiky characteristics. The noise, as observed on an ECG leads, appears as spikes, making the ECG signals difficult to interpret, and these spikes may even be confused as ECG waves themselves. Additionally, a fast Fourier transform applied to the noise to obtain its power spectrum finds component sinusoids at repetition frequencies equal to the impact rate of the rotor rollers on the tubing surface along with higher harmonics. The repetition frequencies are dependent on the number of rollers in a rotor, and are to be distinguished from the rotor rotation rate itself. Further, it has been determined that much of the noise is concentrated at the most proximal electrode and decreases with distal distance, such that the electrodes two to three electrodes downstream from the most proximal are relatively noise free. For example, the noise current takes a least resistive path, closing a circuit with the most proximal electrodes that allows it to "escape" from the relatively high resistance presented by the reduced volume of the irrigation lumen to the relatively low resistance presented by the patient's blood.

Figure 2:
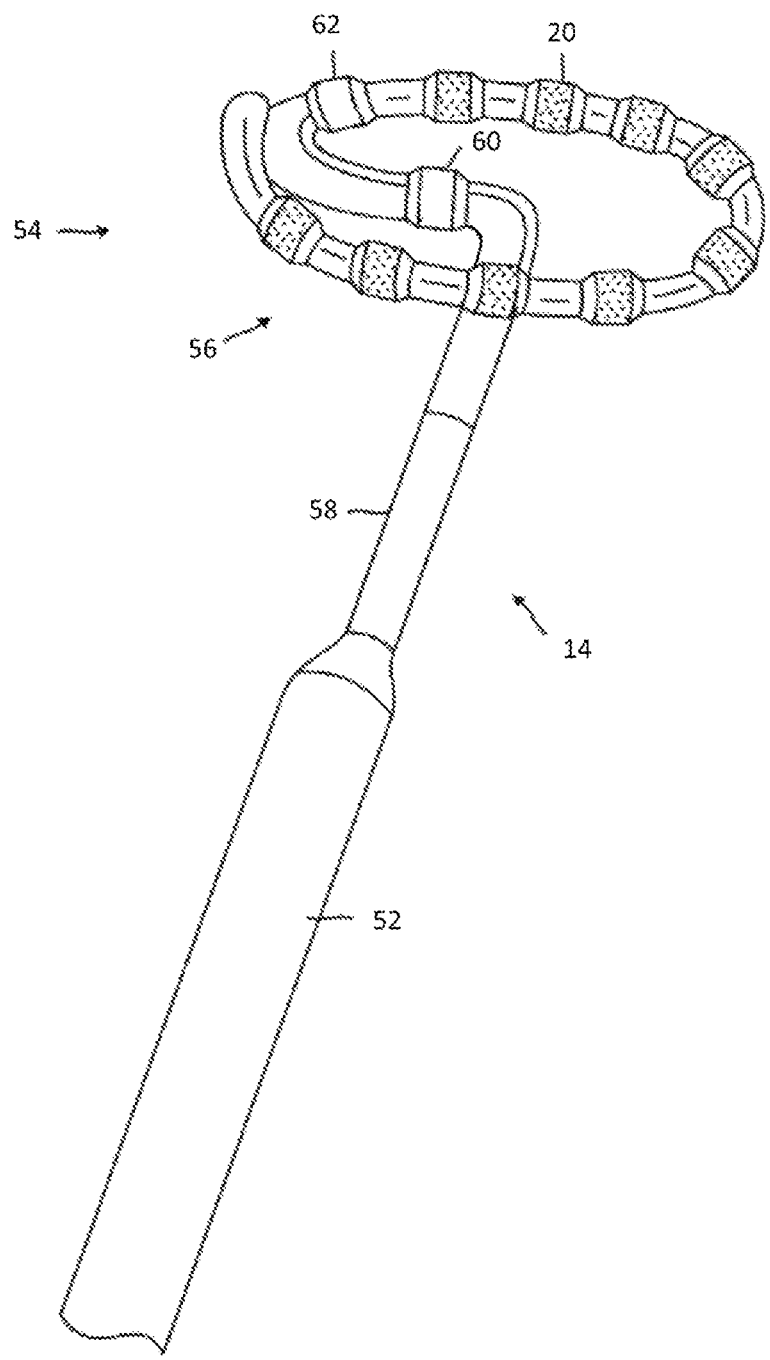
FIG. 2 is a perspective view of a distal end portion of a catheter including an electrode assembly with a shunting electrode, according to one embodiment.

As such, catheter 14 may be designed to incorporate a shunting electrode to provide an electrical connection between the electrically conductive saline and the blood of the patient to help mitigate ECG noise. As shown in FIG. 2, the distal portion of catheter 14 may include an elongated catheter body 52 that extends to handle 18 (not shown in this view) and optionally may be uni- or bi-directionally deflected off axis from the catheter body longitudinal axis for the purpose of steering or guiding the catheter as it is being advanced through the patient's vasculature. In this embodiment, an electrode assembly 54 including a resilient three-dimensional section 56, with electrodes 20 may be disposed distally of a generally straight transitional section 58 at the end of catheter body 52. As shown, three-dimensional section 56, when unconstrained, may have a generally helical form. In other embodiments, electrode assembly 54 may have any desired configuration as warranted, incorporating straight and/or curved portions, and may carry any number of electrodes 20.

A shunting electrode 60 may be positioned proximal to ablation electrodes 20. Shunting electrode 60 may be configured as a ring electrode that is in galvanic or physical contact with the irrigation fluid being supplied by catheter 14. Shunting electrode 60 will also be in galvanic contact with the patient's blood when catheter 14 is deployed in the patient's vasculature. Shunting electrode 60 may be sealed and does not incorporate perforations or other openings. Further, shunting electrode 60 serves only to provide electrical conductivity between the irrigation fluid and the patient's blood, so it is not coupled to cable 28 or any other leads or connectors, and may therefore be considered a "non-functional" electrode. In contrast, ablation electrodes 20 are connected to leads as described above for delivering ablation energy to form a lesion and are termed "functional" electrodes. Similarly, diagnostic or reference electrodes, such as electrode 62, which are not necessarily irrigated, may also be disposed on electrode assembly 54 and provided for recording impendence or electric potentials and/or for providing ECG measurements or any other suitable purpose. Accordingly, electrode(s) 62 also have leads that extend to the proximal end of catheter 14 and are also considered "functional" electrodes. The spacing between shunting electrode 60 and the most proximally located functional electrode may be adjusted as desired to achieve sufficient reduction in ECG noise. In one embodiment, shunting electrode 60 may be spaced approximately the length of 2-3 electrodes 20 or more from the nearest functional electrode. For example, shunting electrode 60 may be positioned at least 6 mm from the most proximal functional electrode. In another aspect, shunting electrode 60 may be positioned at least 3 mm from the most proximal functional electrode. Shunting electrode 60 may reduce ECG noise by providing a low resistance path relative to the higher resistance path represented by the more distal functional electrodes. The surface area of shunting electrode 60 may also be adjusted to achieve the desired noise reduction.

Figure 3:
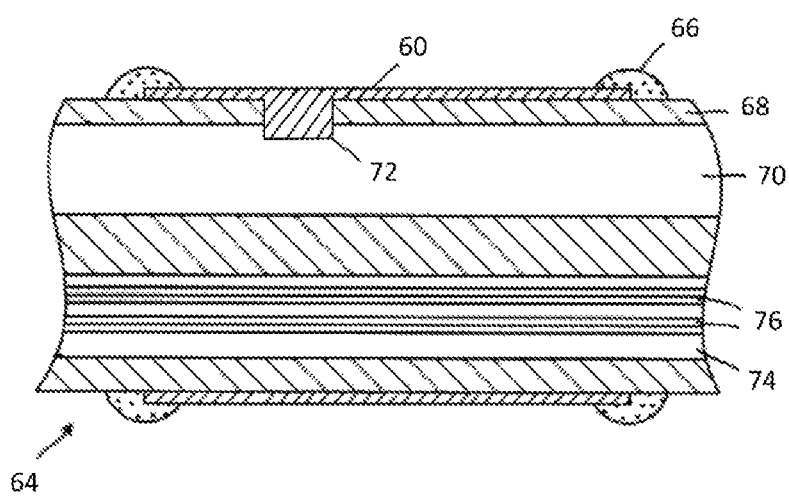
FIG. 3 is a schematic cross sectional view of a shunting electrode, according to one embodiment.

Further details associated with shunting electrode 60 are depicted in the cross sectional view of catheter 14 shown in FIG. 3. The electrode assembly 54 of FIG. 2 may be formed from a tubular member 64. Shunting electrode 60 may be generally cylindrical with a length greater than its diameter. In one embodiment, the length is about 3.0 mm, the outer diameter is about 2.8 mm, and the inner diameter is about 2.33 mm Shunting electrode 60 may have a side cross-section in a barrel-like configuration with a side wall having a thickness, in one embodiment, of about 0.25 mm Shunting electrode 60 may be made of any suitable solid conductive material, such as platinum or gold, preferably a combination of platinum and iridium or gold and platinum, and mounted onto the tubular member 64 with glue 66 or the like. Shunting electrode 60 may extend through the side wall 68 of tubular member 64 into irrigation lumen 70. An interior surface (pad) 72 of shunting electrode may be configured with a desired surface area to provide sufficient galvanic contact with the electrically conductive fluid carried by lumen 70. Shunting electrode 60 may be formed from a single component or separate components that are soldered or otherwise electrically connected. Thus, shunting electrode 60 may be electrically coupled to the irrigation fluid carried by lumen 70. In this construction, tubular member 64 has a second lumen 74 that carries leads 76 that provide electrical communication with one or more electrodes 20 and (optionally) electrode(s) 62 or other sensors or electronics.

In the above embodiments, the catheter 14 has been described in the context of employing a single irrigation lumen 70. However, the techniques of the disclosure may be extended to other designs that incorporate multiple irrigation lumens. In order to dissipate any charge induced the by irrigation pump or other system components, each irrigation lumen may be equipped with a shunting electrode that is located proximal to any functional electrodes supplied by that lumen.

Accordingly, a triboelectric effect or other similar phenomena that occurs in parts of the system 10, particularly where the rotating portions of the pump 48 compress the irrigation tubing 46, may cause an electric charge to propagate downstream. Rather than forming a circuit through electrodes 20 or 62, and returning to the pump 48 via the patient's body, shunting electrode 60 provides a low resistance path for the charge between the irrigation fluid and the blood of the patient, dissipating the charge before it effects the more distally located electrodes 20 and/or 62. Thus, the impact of the generation of a triboelectric charge on the ECG signals may be reduced by employing a design similar to catheter 14. In one aspect, noise in the ECG signal may be suppressed even when employing flow rates in excess of 30 ml/min. For example, the techniques of this disclosure provide reduced ECG noise even when flow rates of 60 ml/min are employed as may be required for catheters having multiple ablation electrodes.

Catheter body 52 comprises an elongated tubular construction and may be flexible, i.e., bendable, but substantially non-compressible along its length. The catheter body 52 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 52 so that, when the control handle 18 is rotated, the distal end of the catheter body will rotate in a corresponding manner. The outer diameter of the catheter body 52 is not critical, but generally should be as small as possible and may be no more than about 10 french depending on the desired application and may be in the range of 7 to 8 french or smaller. Likewise, the thickness of the outer wall is not critical, but may be thin enough so that any necessary lumens can accommodate the irrigation fluid, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends, an irrigation lumen extending through the elongated catheter body, the irrigation lumen containing irrigation fluid, the irrigation fluid connected to an irrigation fluid source, and an electrode assembly at the distal end of the elongated catheter body, the electrode assembly comprising a functional electrode located at a first position on the electrode assembly, the functional electrode being electrically coupled to at least one lead, and a non-functional shunting electrode located proximal to the first position, wherein the shunting electrode is configured to be electrically coupled to irrigation fluid contained within the irrigation lumen and only to provide electrical conductivity between the irrigation fluid and a patient's blood, wherein the shunting electrode is not connected to or energized by an energy source.

2. The catheter of claim 1, wherein the functional electrode is an irrigated electrode supplied with irrigation fluid by the irrigation lumen.

3. The catheter of claim 2, wherein the electrode assembly comprises a plurality of irrigated electrodes located distally of the first position.

4. The catheter of claim 3, wherein the electrode assembly further comprises at least one additional functional electrode located distally of the shunting electrode.

5. The catheter of claim 3, wherein the shunting electrode is spaced a distance that equals the length of at least two of the irrigated electrodes from the first position.

6. The catheter of claim 1, wherein the shunting electrode is spaced a distance of at least 6 mm from the first position.

7. The catheter of claim 1, wherein the shunting electrode is electrically coupled to a pad disposed within the irrigation lumen.

* * * * *